United States Patent
Lu

(10) Patent No.: US 10,918,806 B2
(45) Date of Patent: Feb. 16, 2021

(54) SAFE SYRINGE

(71) Applicant: Wen-Chin Lu, Taipei (TW)

(72) Inventor: Wen-Chin Lu, Taipei (TW)

( * ) Notice: Subject to any disclaimer, the term of this patent is extended or adjusted under 35 U.S.C. 154(b) by 292 days.

(21) Appl. No.: 16/068,216

(22) PCT Filed: Dec. 26, 2016

(86) PCT No.: PCT/CN2016/112099
§ 371 (c)(1),
(2) Date: Jul. 5, 2018

(87) PCT Pub. No.: WO2017/118308
PCT Pub. Date: Jul. 13, 2017

(65) Prior Publication Data
US 2019/0038847 A1 Feb. 7, 2019

(30) Foreign Application Priority Data
Jan. 8, 2016 (CN) .......................... 201610012305.3

(51) Int. Cl.
*A61M 5/178* (2006.01)
*A61M 5/32* (2006.01)
(Continued)

(52) U.S. Cl.
CPC .......... *A61M 5/3221* (2013.01); *A61M 5/178* (2013.01); *A61M 5/348* (2013.01);
(Continued)

(58) Field of Classification Search
CPC ................ A61M 5/3221; A61M 5/178; A61M 2005/323; A61M 2005/31516;
(Continued)

(56) References Cited

U.S. PATENT DOCUMENTS

| | | | | |
|---|---|---|---|---|
| 2002/0117515 A1* | 8/2002 | Lee | ...................... | A61M 5/3216 222/137 |
| 2003/0093038 A1* | 5/2003 | Chiang | .............. | A61M 5/31511 604/240 |

(Continued)

FOREIGN PATENT DOCUMENTS

| | | |
|---|---|---|
| CN | 200987815 Y | 12/2007 |
| CN | 201020124 Y | 2/2008 |

(Continued)

*Primary Examiner* — Bhisma Mehta
*Assistant Examiner* — Daniel Moore
(74) *Attorney, Agent, or Firm* — Muncy, Geissler, Olds & Lowe, P.C.

(57) ABSTRACT

A safe syringe includes a barrel, a needle seat and a plunger, wherein the needle seat has a hook rod, a linkage deformation portion and a barrel clamping portion; and the plunger has a rod body, and a hook insertion hole which can be sleeved with the hook rod of the needle seat and compress the linkage deformation portion for elastic deformation such that the barrel clamping portion of the needle seat is not clamped into the seat clamping slot of the barrel, and the hook insertion hole can hook the hook rod of the needle seat to move the needle seat. The safe syringe can allow stable positioning and quick pullback of the needle seat and effectively reduce liquid medicine residue.

11 Claims, 19 Drawing Sheets

(51) Int. Cl.
 *A61M 5/315* (2006.01)
 *A61M 5/34* (2006.01)
(52) U.S. Cl.
 CPC .............. *A61M 2005/31516* (2013.01); *A61M 2005/323* (2013.01); *A61M 2005/3206* (2013.01); *A61M 2005/3224* (2013.01); *A61M 2005/3231* (2013.01)
(58) Field of Classification Search
 CPC .......... A61M 2005/3231; A61M 5/348; A61M 2005/3206; A61M 2005/3224; A61M 5/50; A61M 5/3232
 See application file for complete search history.

(56) References Cited

U.S. PATENT DOCUMENTS

| | | |
|---|---|---|
| 2006/0106339 A1 | 5/2006 | Mastorakis |
| 2010/0100053 A1* | 4/2010 | Chang .................... A61M 5/322 604/194 |
| 2015/0005706 A1* | 1/2015 | Diaz ................. A61M 5/31505 604/110 |

FOREIGN PATENT DOCUMENTS

| | | |
|---|---|---|
| CN | 101474443 A | 7/2009 |
| CN | 101530645 A | 9/2009 |
| CN | 205460212 U | 8/2016 |
| WO | WO2005023344 A1 | 3/2005 |
| WO | WO2009105960 A1 | 9/2009 |

* cited by examiner

US 10,918,806 B2

SAFE SYRINGE

FIELD OF THE INVENTION

The invention relates to a medical device and particularly to a Safe Syringe.

BACKGROUND OF THE INVENTION

A conventional Safe Syringe, for example, in US Patent Publication US20060106339, still has the problems of uncertainty in fixing and pullback of a needle seat as well as a larger amount of liquid medicine residue.

Accordingly, the disadvantages of the known Safe Syringe are yet to be improved.

SUMMARY OF THE INVENTION

In view of the above problems, a main object of the invention is to provide a Safe Syringe which can allow stable positioning of a needle seat, facilitate quick pullback of the needle seat and effectively reduce liquid medicine residue.

To achieve the above object, the invention provides a Safe Syringe, comprising: a barrel having a barrel body, an accommodating chamber, a seat mounting hole and a seat clamping slot; a needle seat having a seat body mounted in the seat mounting hole of the barrel, a needle hole, a hook rod, a linkage deformation portion connected to the hook rod, and a barrel clamping portion connected to the linkage deformation portion, linked thereby and capable of being clamped into the seat clamping slot of the barrel; and a plunger having a rod body, and a hook insertion hole which is capable of being sleeved with the hook rod of the needle seat and compressing the linkage deformation portion for elastic deformation such that the barrel clamping portion of the needle seat is not clamped into the seat clamping slot of the barrel, wherein the hook insertion hole is capable of hooking the hook rod of the needle seat to move the needle seat.

The needle seat has a recessed chamber which is communicated with the needle hole and the linkage deformation portion.

The needle seat has a flow guiding surface connected to the recessed chamber.

The needle seat has an internally retracted surface corresponding to the linkage deformation portion.

A vertical distance L1 from a centerline of the needle seat to an outer edge of the hook rod is smaller than a vertical distance L2 from the centerline of the needle seat to an outer edge of the linkage deformation portion.

The barrel clamping portion is connected with the linkage deformation portion by extending a certain length.

The Safe Syringe further comprises a sealing ring R arranged between the barrel and the needle seat.

The barrel has a main barrel and a front sleeve sleeved on the main barrel.

As a further improvement of the invention, toothed structures are arranged on corresponding end faces of the front sleeve and the main barrel, and the toothed structure on the end face of the front sleeve is engaged with the toothed structure on the end face of the main barrel. Rotation between the front sleeve and the main barrel can be prevented.

The Safe Syringe further comprises a sealing ring R arranged between the front sleeve and the seat body of the needle seat.

The barrel has a counterbore, and the needle seat has a seat shoulder cooperatively positioned in the counterbore of the barrel.

By employing the above technical solutions, the Safe Syringe provided by the invention can indeed allow stable positioning of the needle seat, facilitate quick pullback of the needle seat and effectively reduce liquid medicine residue.

DETAILED DESCRIPTION OF THE INVENTION

Figure 1:
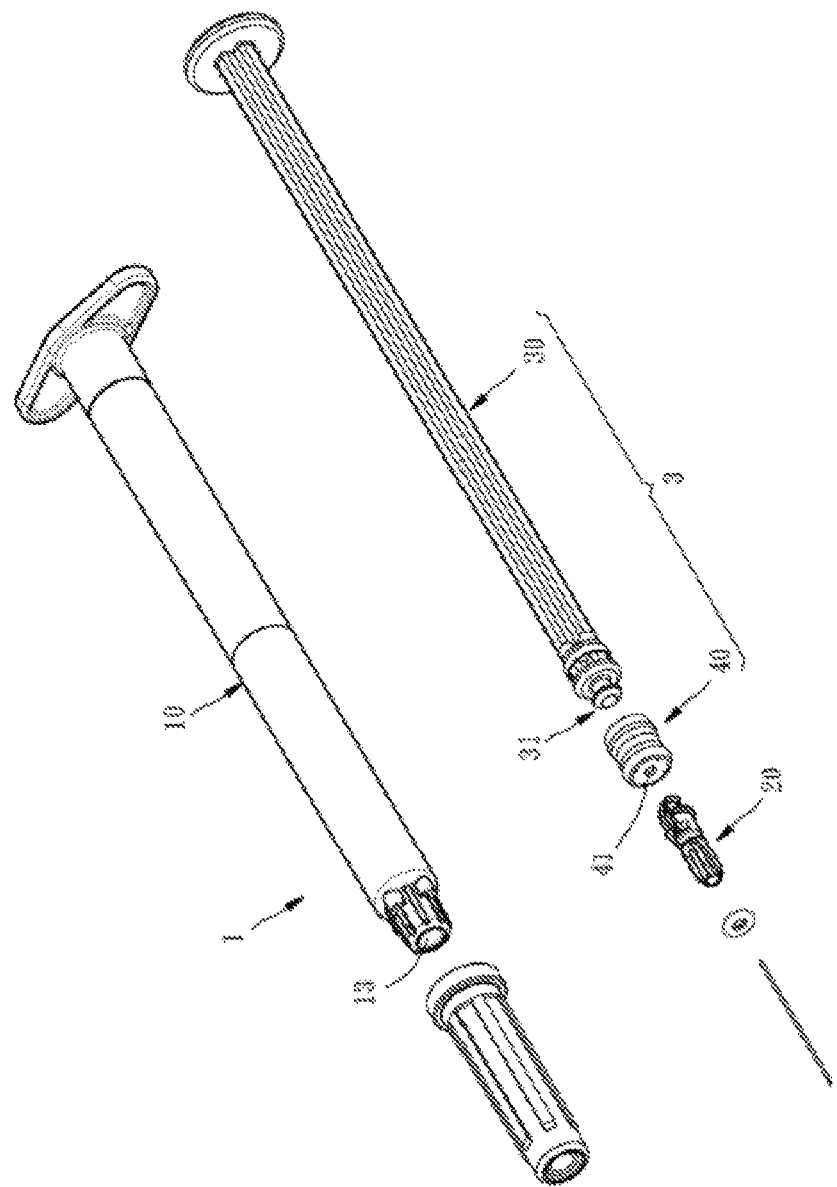
FIG. 1 is a perspective view of one preferred embodiment of the invention.

The following embodiments will be listed with reference to the accompanying drawings to describe the structure and efficacy of the invention in detail.

The applicant first illustrates here that all adjectives related to directionality, such as inner, outer, upper and lower, which are mentioned throughout the description, are based on the directions in the drawings of the invention.

The technical contents and features of the invention will be described below in detail by the listed embodiments in conjunction with the accompanying drawings.

As shown in FIGS. 1 to 4, a Safe Syringe according to one preferred embodiment of the invention comprises the following components.

In this embodiment, a main barrel 10 alone can form a barrel 1; i.e. in a broad sense, the Safe Syringe of the invention comprises a barrel 1 having a main barrel 10.

The main barrel 10 has a barrel body 11, an accommodating chamber 12 communicated with a seat mounting hole 13, a seat clamping slot 14 located at an inner edge of the seat mounting hole 13, and a counterbore 15 arranged between the accommodating chamber 12 and the seat clamping slot 14.

Figure 2:
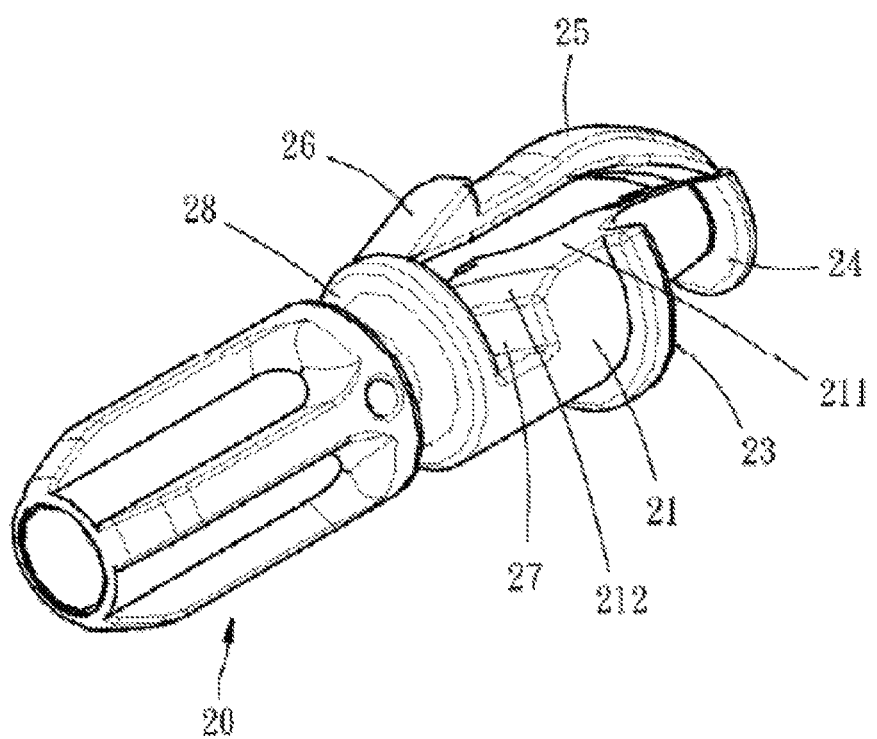
FIG. 2 is a sectional view showing one operating state of one preferred embodiment of the invention.
Figure 3:
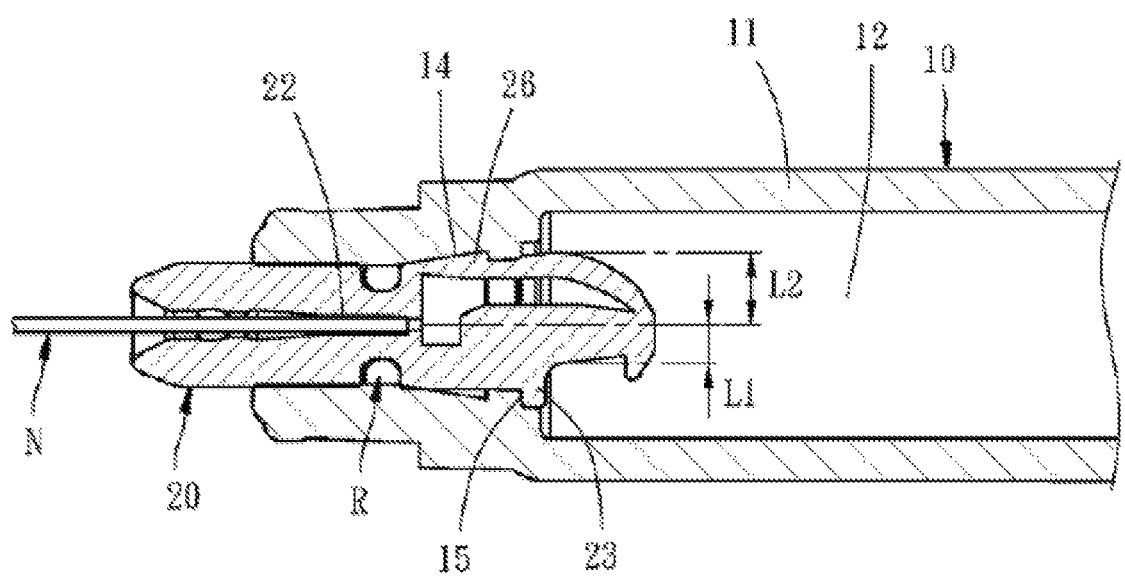
FIG. 3 is a sectional view showing another operating state of one preferred embodiment of the invention.
Figure 4:
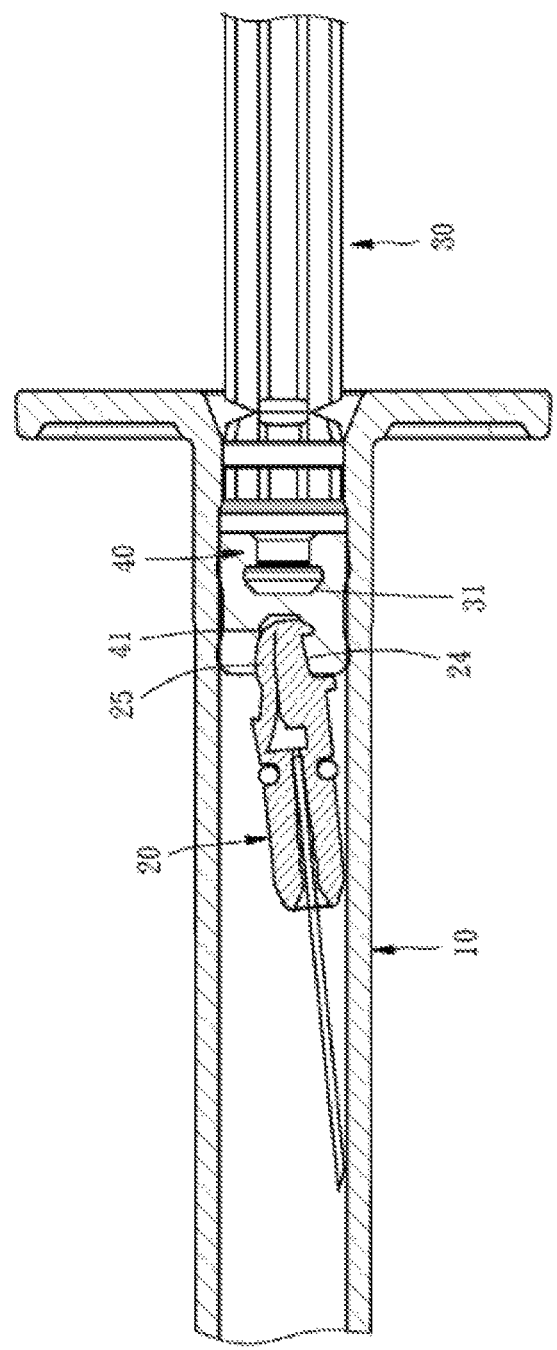
FIG. 4 is a perspective view of a needle seat of one preferred embodiment of the invention.
Figure 5:
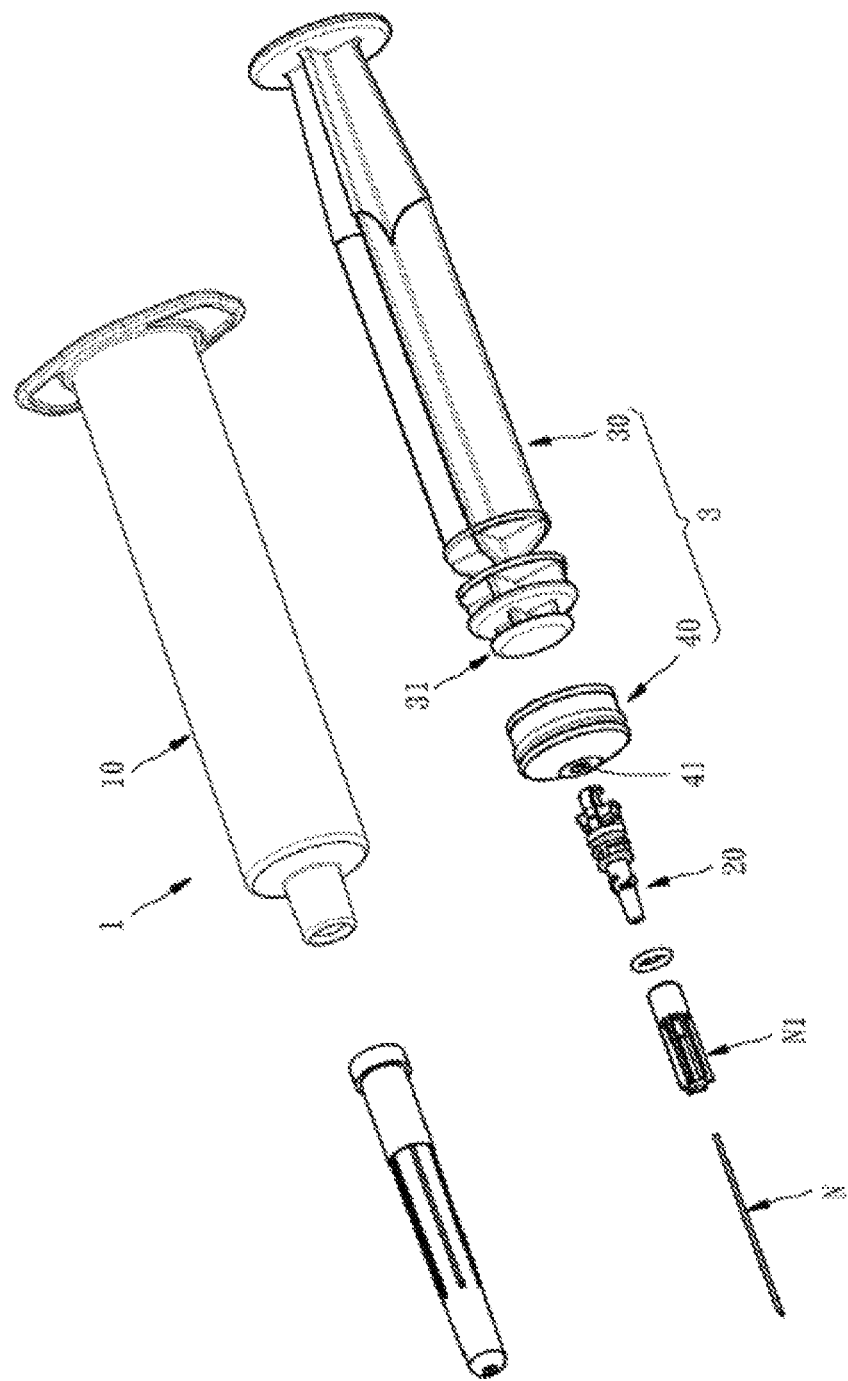
FIG. 5 is a perspective view of another preferred embodiment of the invention.
Figure 6:
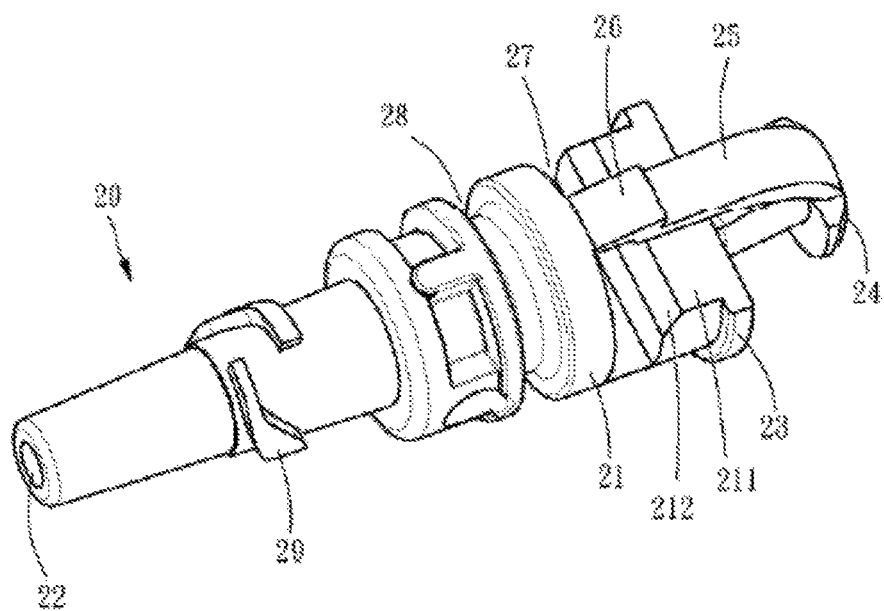
FIG. 6 is a sectional view showing one operating state of another preferred embodiment of the invention.
Figure 7:
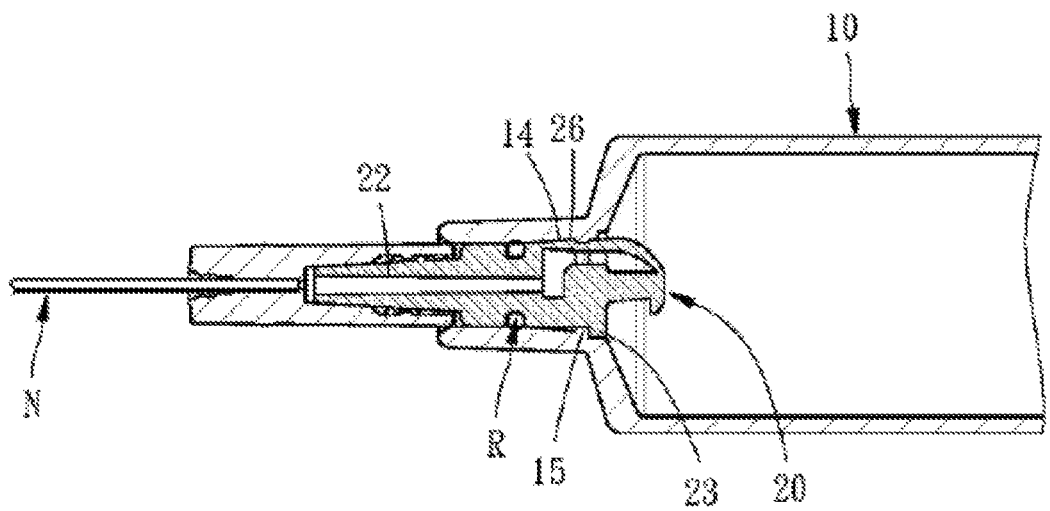
FIG. 7 is a sectional view showing another operating state of another preferred embodiment of the invention.
Figure 8:
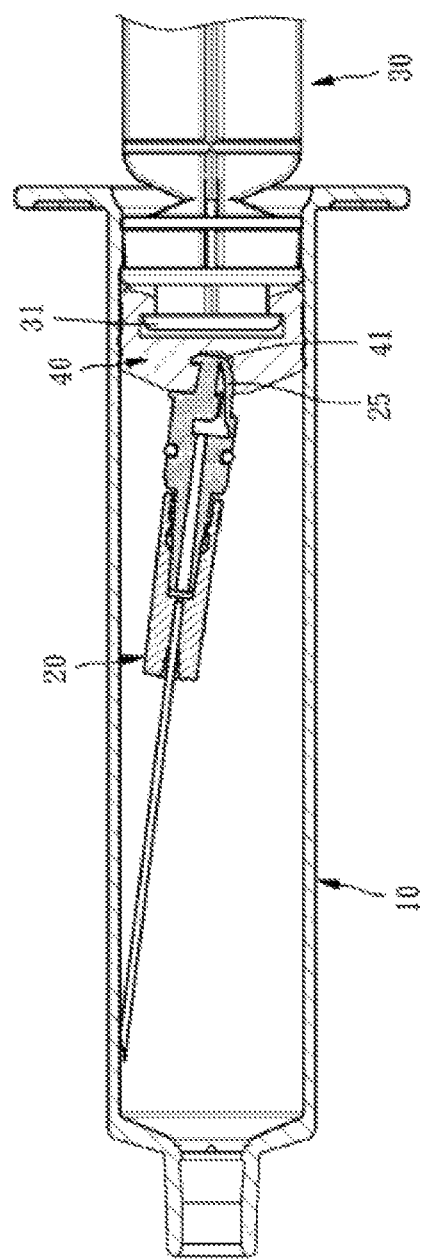
FIG. 8 is a perspective view of a needle seat of another preferred embodiment of the invention.
Figure 9:
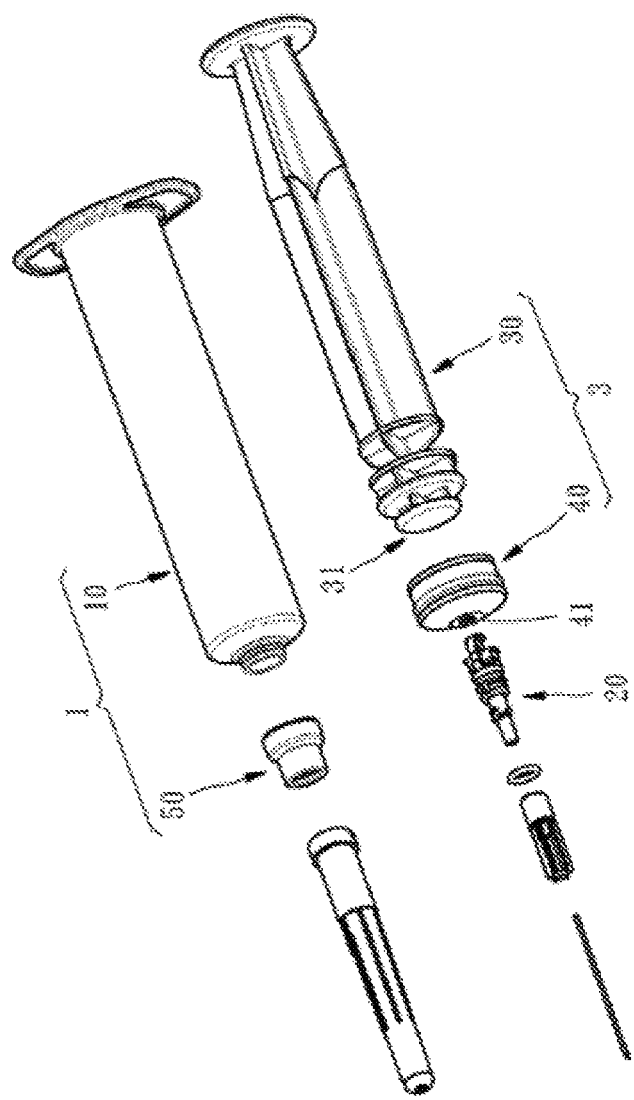
FIG. 9 is a perspective view of still another preferred embodiment of the invention.
Figure 10:
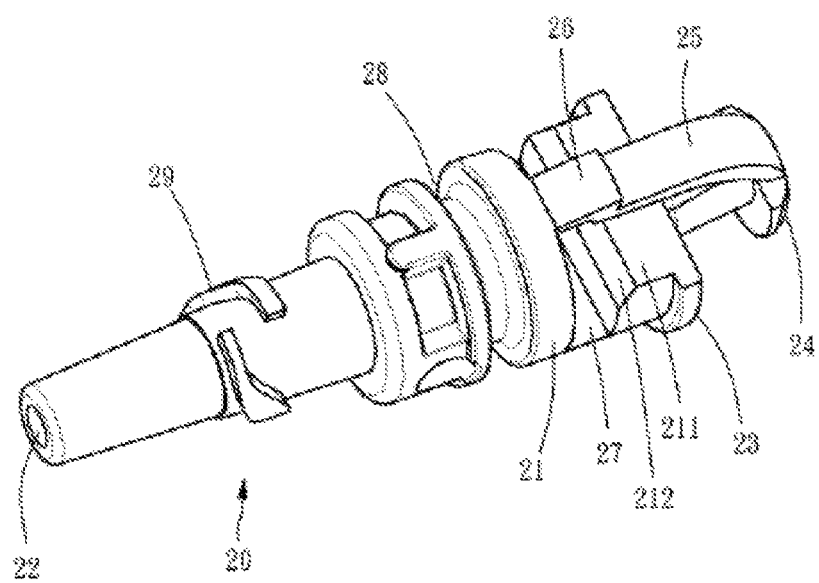
FIG. 10 is a sectional view showing one operating state of still another preferred embodiment of the invention.
Figure 11:
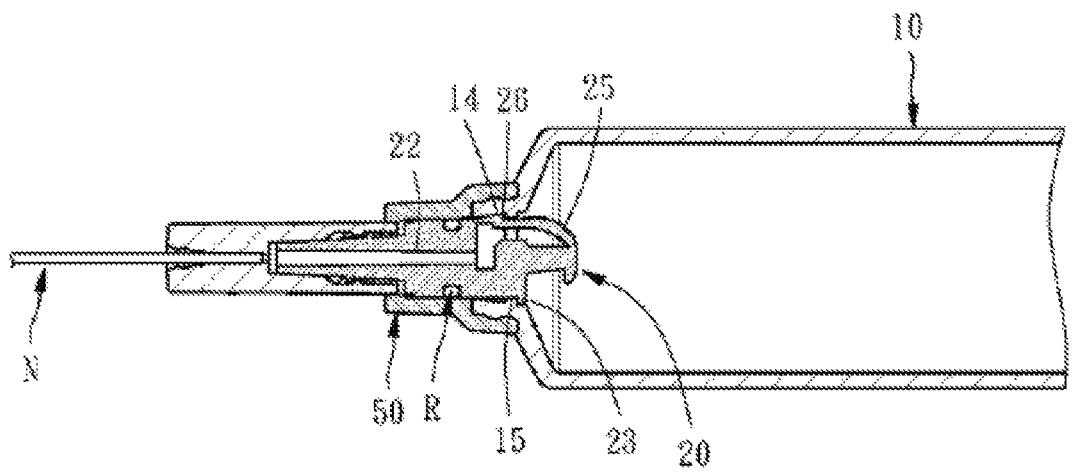
FIG. 11 is a sectional view showing another operating state of still another preferred embodiment of the invention.
Figure 12:
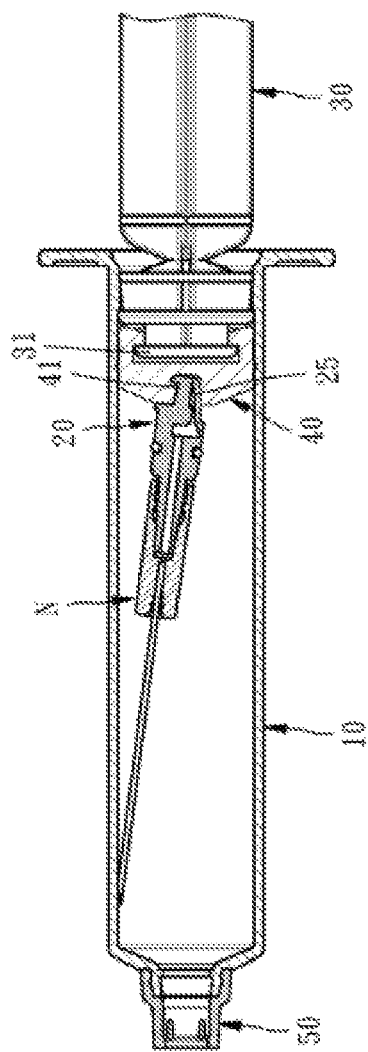
FIG. 12 is a perspective view of a needle seat of still another preferred embodiment of the invention.
Figure 13:
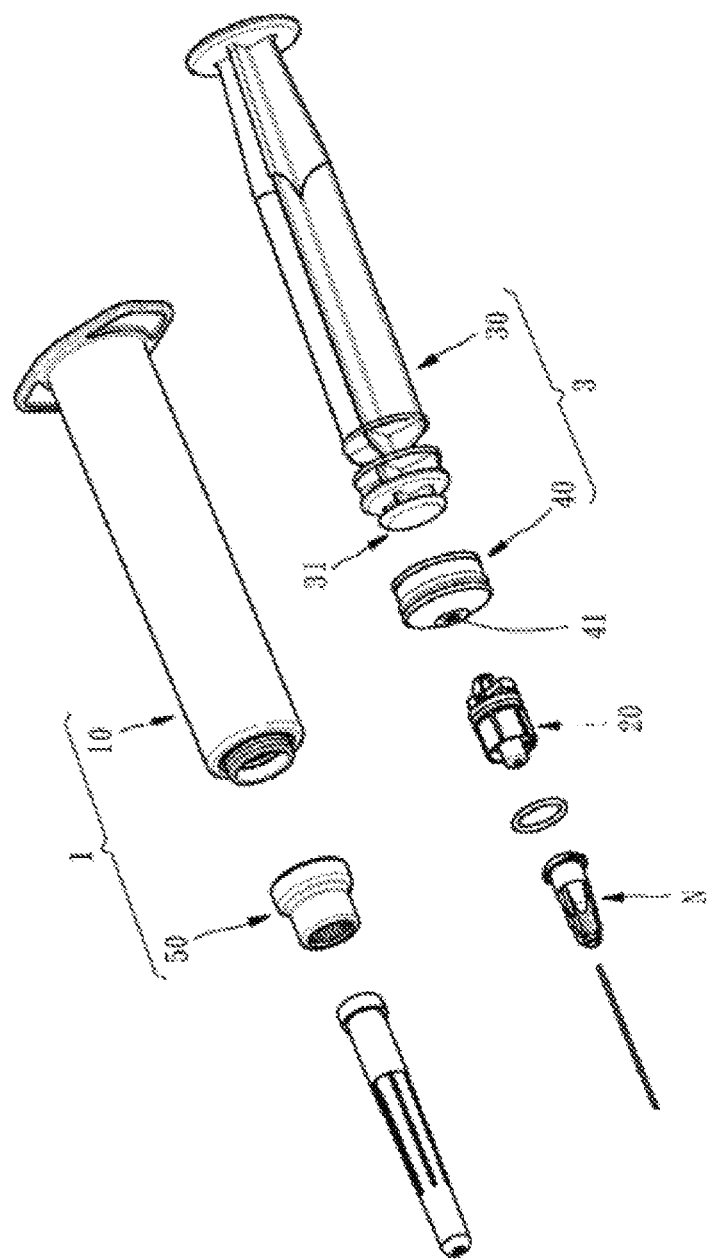
FIG. 13 is a perspective view of still further preferred embodiment of the invention.
Figure 14:
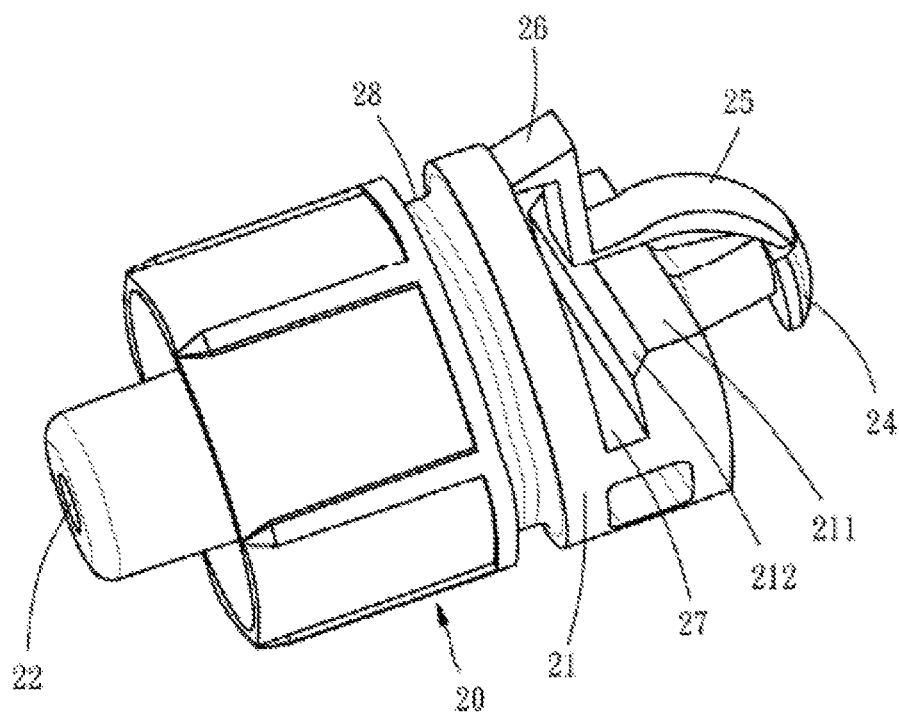
FIG. 14 is a sectional view showing one operating state of still further preferred embodiment of the invention.
Figure 15:
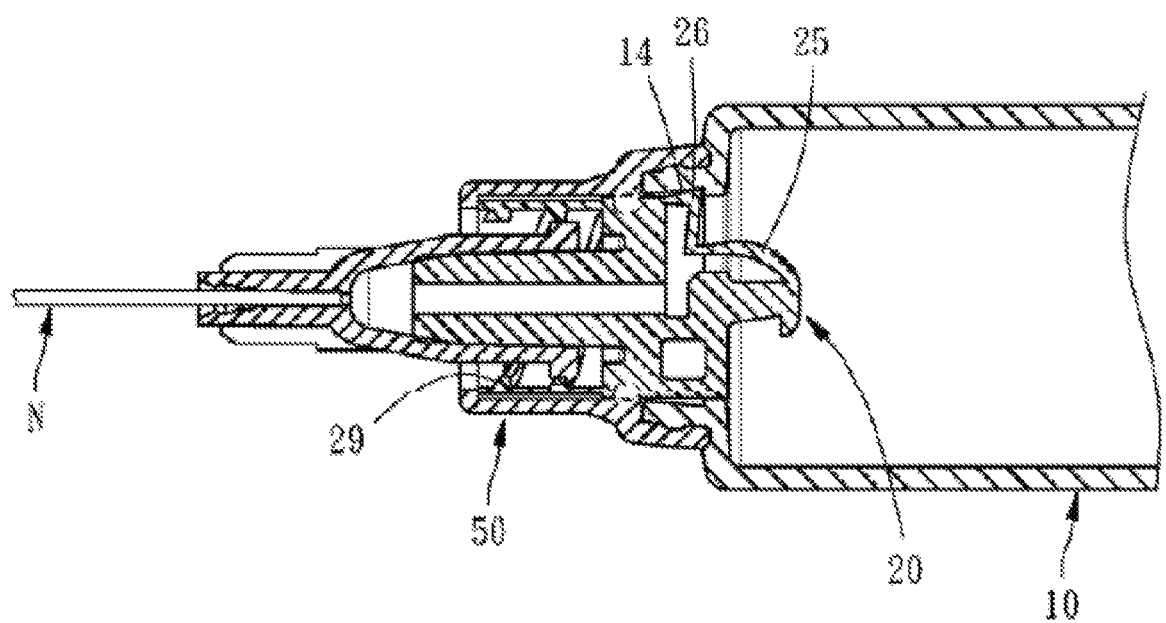
FIG. 15 is a sectional view showing another operating state of still further preferred embodiment of the invention.
Figure 16:
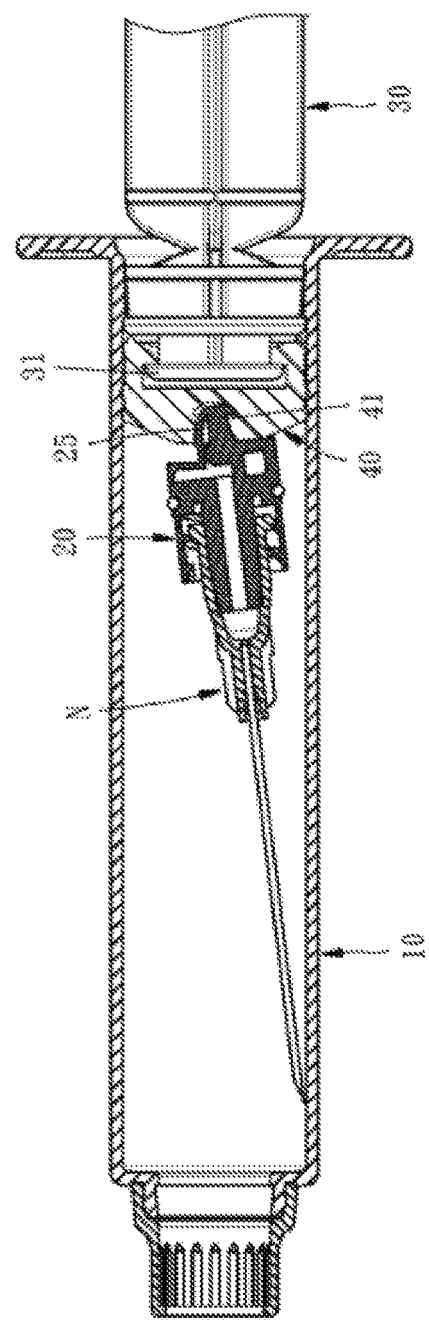
FIG. 16 is a perspective view of a needle seat of still further preferred embodiment of the invention.
Figure 17:
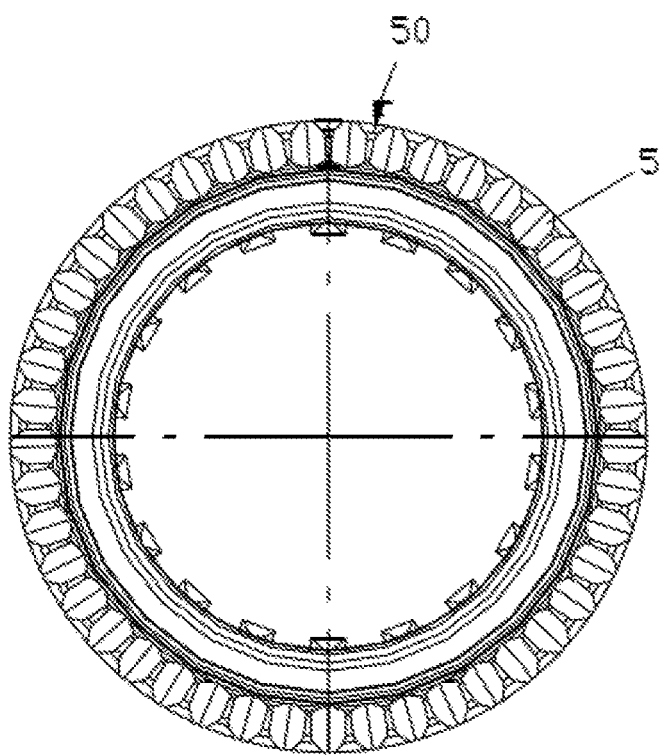
FIG. 17 is a side view of a front sleeve of still further preferred embodiment of the invention.
Figure 18:
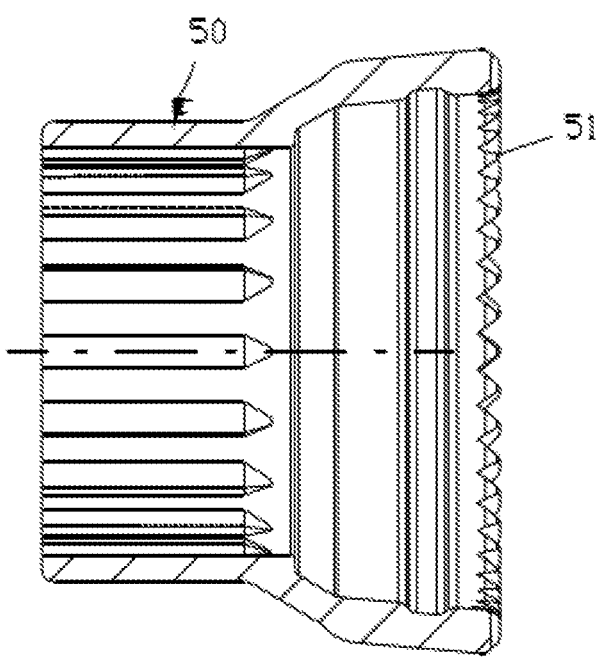
FIG. 18 is a front view of a front sleeve of still further preferred embodiment of the invention.
Figure 19:
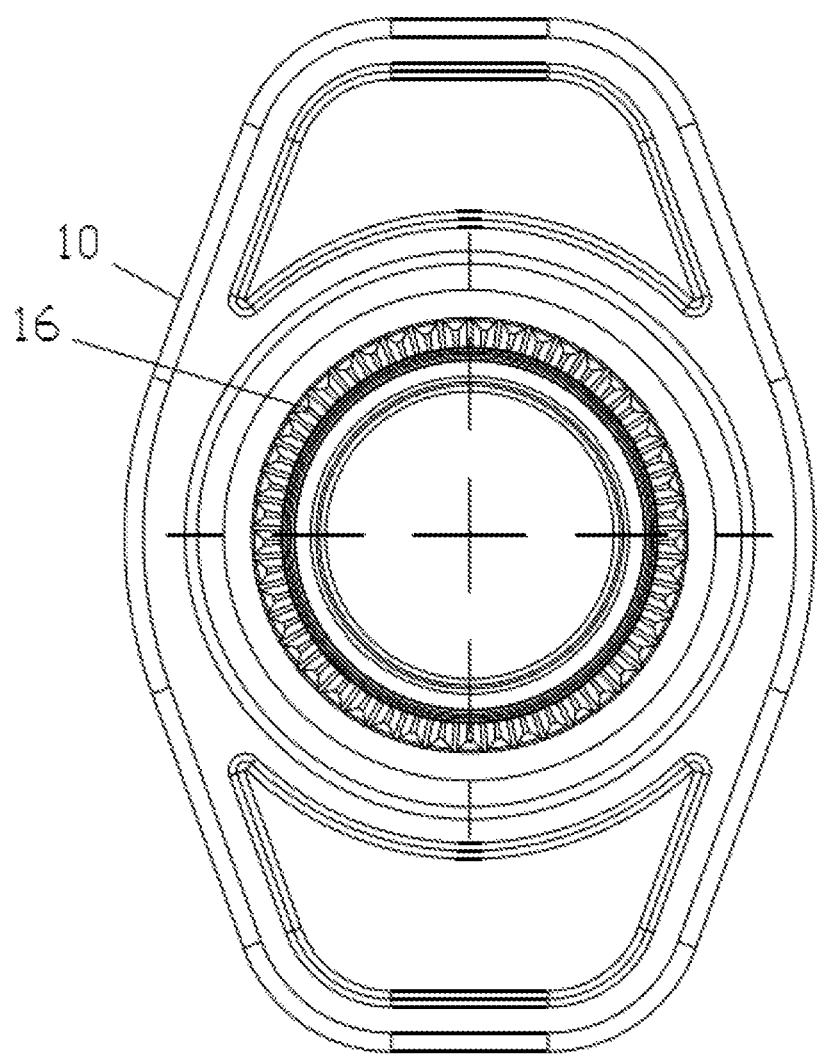
FIG. 19 is a side view of a main barrel of still further preferred embodiment of the invention.

A needle seat 20 has a seat body 21 mounted in the seat mounting hole 13 of the main barrel 10, a needle hole 22, a seat shoulder 23 cooperatively positioned in the counterbore 15 of the barrel 1, a hook rod 24 having a preferred slightly tapered rod body, a linkage deformation portion 25 in the shape of a convex arc-shaped sheet and connected to the hook rod 24, and a barrel clamping portion 26 connected to the linkage deformation portion 25, linked thereby and capable of being clamped into the seat clamping slot 14 of the barrel 1. The hook rod 24 is mounted at a tail of the linkage deformation portion 25 so that the linkage deformation portion 25 and the hook rod 24 form an asymmetrical one-sided arc structure as shown in FIG. 2 and FIG. 3.

The needle seat 20 also has an internally retracted surface 211 correspondingly cooperating with the linkage deformation portion 25; i.e. a slightly excavated surface is formed at a position of the seat body 21 and/or the hook rod 24 corresponding to the linkage deformation portion 25 to provide the linkage deformation portion 25 with more deformation space.

The needle seat 20 also has a recessed chamber 27 opened between the needle hole 22 and the linkage deformation portion 25. The needle seat 20 also has an annular groove 28 which can be equipped with a sealing ring R for sealing between the barrel 1 and the needle seat 20.

The needle seat 20 also has a flow guiding surface 212 connected to the recessed chamber 27, the flow guiding surface 212 is also connected to the internally retracted surface 211, and the flow guiding surface can allow liquid medicine to more easily flow to the recessed chamber 27.

In addition, the other end of the barrel clamping portion 26 is also connected to the seat body 21 of the needle seat.

In this embodiment, the needle seat 20 is equipped with a needle N in the needle hole 22 thereof.

In this embodiment, a vertical distance L1 from a centerline of the needle seat 20 to an outer edge of the hook rod 24 is smaller than a vertical distance L2 from the centerline of the needle seat 20 to an outer edge of the linkage deformation portion 25.

A plunger 3 has a push rod 30 with a rod body 31, and a sealing plug 40 connected to the rod body 31 of the push rod 30.

The sealing plug 40 has a hook insertion hole 41 which can be sleeved with the hook rod 24 of the needle seat 20 and compress the linkage deformation portion 25 for elastic deformation such that the barrel clamping portion 26 of the needle seat 20 is not clamped into the seat clamping slot 14 of the barrel 1, and the hook insertion hole 41 can hook the hook rod 24 of the needle seat 20 to move the needle seat 20.

The barrel clamping portion 26 of the needle seat 20 can be effectively engaged with the seat clamping slot 14 of the barrel 1.

When the plunger 3 is pushed forward such that the hook insertion hole 41 of the sealing plug 40 thereof is sleeved into the hook rod 24 and the linkage deformation portion 25 of the needle seat 20, the barrel clamping portion 26 of the needle seat 20 can be controlled to disengage from the seat clamping slot 14 of the barrel 1, thus enabling successful pullback. When the linkage deformation portion 25 is elastically deformed, the voids between the linkage deformation portion and the seat body 21 as well as the hook rod 24 become small, thus liquid medicine residue therebetween can be reduced.

Finally, the needle seat 20 and the needle N are also tilted to one side due to the cooperation relation between the linkage deformation portion 25 of the needle seat 20 and the hook insertion hole 41 of the plunger 3, thus the needle seat 20 and the needle N are not easily pushed out of the barrel 1.

This embodiment can thus achieve the object of the invention.

The focus of the invention further lies in that the design of cooperation between the linkage deformation portion 25 and the recessed chamber 27 of the needle seat 20 can also effectively reduce the residual amount of the injected liquid medicine.

As shown in FIGS. 5 to 8, the invention provides a Safe Syringe of another embodiment, which is substantially the same as the foregoing embodiment, with the main difference below.

The needle seat 20 also has a needle connecting portion 29 formed at a front section thereof.

The needle N is arranged at a connecting member N1. The connecting member N1 is further connected to the needle connecting portion 29 of the needle seat 20.

Similarly, this embodiment can thus achieve the object of the invention.

As shown in FIGS. 9 to 12, a Safe Syringe according to another preferred embodiment of the invention is substantially the same as the foregoing embodiment, with the main difference below.

The barrel 1 has a main barrel 10 and a front sleeve 50 which can be hermetically sleeved on the main barrel 10 to together form a seat mounting hole 13, and the sealing ring R is arranged between the front sleeve 50 and the seat body 21 of the needle seat 20.

That is, the main barrel 10 also has a front sleeve 50 sleeved at a front end of the main barrel 10. In this embodiment, the seat clamping slot 14 and the counterbore 15 are formed on the main barrel 10, and of course, can also be formed on the front sleeve 50 instead. The use of a combination of two members can make it easier to manufacture the barrel 1 and can increase its use forms.

Similarly, this embodiment can thus achieve the object of the invention.

As shown in FIGS. 13 to 19, a Safe Syringe according to another preferred embodiment of the invention is substantially the same as the foregoing embodiment, with the main difference below.

The needle seat 20 has a larger size and an outer barrel portion is formed additionally to be equipped with the needle N.

The barrel clamping portion 26 can extend a certain length and then is connected with the linkage deformation portion 25. Accordingly, the hook insertion hole 41 of the sealing plug 40 can still compress the linkage deformation portion 25 of the needle seat 20 for elastic deformation to drive the engagement and disengagement of the barrel clamping portion 26.

Similarly, this embodiment can thus achieve the object of the invention.

The push rod 30 and the sealing plug 40 of the invention may be either combined or integral.

In addition to being a separate member as described above, the sealing ring R of the invention can also be integrally formed on the barrel 1 or the needle seat 20.

When the Safe Syringe of this embodiment is mounted, the front sleeve 50 is first mounted at a front end of the main barrel 10, the needle seat 20 is disposed at the front end of the main barrel 10 from a rear end of the main barrel 10, the linkage deformation portion 25 of the needle seat 20 is clamped into the seat clamping slot 14 of the main barrel 10, the connecting member N1 is then mounted at a front end of the needle seat 20, the needle N is then mounted on the connecting member N1, and the connecting member N1 is screwed to the needle seat 20 during its mounting. Since the front sleeve 50 is sleeved with the main barrel 10, relative rotation may occur therebetween such that the connecting member N1 cannot be tightly locked on the needle seat 20. To solve this problem, toothed structures 51 and 16 which cooperate with each other can be arranged on corresponding end faces of the front sleeve 50 and the main barrel 10, and the toothed structure 51 on the end face of the front sleeve 50 is engaged with the toothed structure 16 on the end face of the main barrel 10. In this way, when the connecting member N1 is rotatably mounted, the front sleeve 50 and the main barrel 10 do not rotate such that the connecting member N1 can be tightly locked on the needle seat 20 and then the needle N can be tightly locked.

Any of the embodiments described above can be used alone or in combination with each other to achieve the object of the invention.

In summary, the Safe Syringe provided by the invention can indeed allow stable positioning of the needle seat, facilitate quick pullback of the needle seat and effectively reduce liquid medicine residue, thus achieving the object of the invention indeed.

The above embodiments are only for the purpose of describing the technical concept and features of the invention, and aim at enabling the persons skilled in the art to understand and implement the contents of the invention, and therefore cannot limit the protection scope of the invention. Any equivalent change or modification made based on the spirit and essence of the invention shall be covered within the protection scope of the invention.

The invention claimed is:

1. A safe syringe, comprising:
   a barrel having a barrel body, an accommodating chamber, a seat mounting hole and a seat clamping slot;
   a needle seat having a seat body mounted in the seat mounting hole of the barrel, a needle hole, a hook rod, a linkage deformation portion connected to the hook rod, and a barrel clamping portion connected to the linkage deformation portion, linked thereby and capable of being clamped into the seat clamping slot of the barrel; and
   a plunger having a rod body, and a hook insertion hole which is capable of being sleeved with the hook rod of the needle seat and compressing the linkage deformation portion for elastic deformation such that the barrel clamping portion of the needle seat is not clamped into the seat clamping slot of the barrel, the hook insertion hole being capable of hooking the hook rod of the needle seat to move the needle seat,
   wherein the hook rod is mounted at a tail of the linkage deformation portion so that the linkage deformation portion and the hook rod form an asymmetrical one-sided arc structure.

2. The safe syringe according to claim 1, wherein the needle seat has a recessed chamber which is communicated with the needle hole and the linkage deformation portion.

3. The safe syringe according to claim 1, wherein the needle seat has a flow guiding surface connected to a recessed chamber.

4. The safe syringe according to claim 1, wherein the needle seat has an internally retracted surface corresponding to the linkage deformation portion.

5. The safe syringe according to claim 1, wherein a vertical distance from a centerline of the needle seat to an outer edge of the hook rod is smaller than a vertical distance from the centerline of the needle seat to an outer edge of the linkage deformation portion.

6. The safe syringe according to claim 1, wherein the barrel clamping portion is connected with the linkage deformation portion by extending a certain length.

7. The safe syringe according to claim 1, further comprising a sealing ring arranged between the barrel and the needle seat.

8. The safe syringe according to claim 1, wherein the barrel has a main barrel and a front sleeve sleeved on the main barrel.

9. The safe syringe according to claim 8, wherein toothed structures are arranged on corresponding end faces of the front sleeve and the main barrel, and the toothed structure on the end face of the front sleeve is engaged with the toothed structure on the end face of the main barrel.

10. The safe syringe according to claim 8, further comprising a sealing ring arranged between the front sleeve and the seat body of the needle seat.

11. The safe syringe according to claim 1, wherein the barrel has a counterbore, and the needle seat has a seat shoulder cooperatively positioned in the counterbore of the barrel.

* * * * *